United States Patent
Marcoux et al.

(10) Patent No.: US 11,022,550 B2
(45) Date of Patent: Jun. 1, 2021

(54) METHOD FOR OBSERVING ORGANISMS AND ASSOCIATED SYSTEM

(71) Applicants: Commissariat à l'énergie atomique et aux énergies alternatives, Paris (FR); bioMérieux, Marcy l'Etoile (FR)

(72) Inventors: Pierre Marcoux, Saint Egreve (FR); Mathieu Dupoy, Grenoble (FR)

(73) Assignees: COMMISSARIAT A L'ENERGIE ATOMIQUE ET AUX ENERGIES ALTERNATIVES, Paris (FR); BIOMERIEUX, L'Etoile (FR)

( * ) Notice: Subject to any disclaimer, the term of this patent is extended or adjusted under 35 U.S.C. 154(b) by 513 days.

(21) Appl. No.: 14/891,820

(22) PCT Filed: May 19, 2014

(86) PCT No.: PCT/EP2014/060263
§ 371 (c)(1),
(2) Date: Nov. 17, 2015

(87) PCT Pub. No.: WO2014/184390
PCT Pub. Date: Nov. 20, 2014

(65) Prior Publication Data
US 2016/0103064 A1  Apr. 14, 2016

(30) Foreign Application Priority Data

May 17, 2013 (FR) ...................................... 13 54476

(51) Int. Cl.
*G01N 21/47* (2006.01)
*C12Q 1/18* (2006.01)
*C12Q 1/02* (2006.01)

(52) U.S. Cl.
CPC .......... *G01N 21/4788* (2013.01); *C12Q 1/02* (2013.01); *C12Q 1/18* (2013.01)

(58) Field of Classification Search
CPC .... G01N 21/4788; G01N 33/186; C12Q 1/02; C12Q 1/18
USPC ............................................ 356/601; 435/29
IPC ............ G01N 21/47,33/18; C12Q 1/02; G01B 11/24
See application file for complete search history.

(56) References Cited

U.S. PATENT DOCUMENTS

| | | | |
|---|---|---|---|
| 3,928,140 A | 12/1975 | Wyatt et al. | |
| 7,016,523 B1 | 3/2006 | Ogawa | |
| 7,582,415 B2 * | 9/2009 | Straus | B82Y 20/00 435/287.1 |
| 2003/0082516 A1 | 5/2003 | Straus | |
| 2003/0143580 A1 | 7/2003 | Straus | |
| 2003/0170613 A1 | 9/2003 | Straus | |
| 2006/0172370 A1 | 8/2006 | Hirleman et al. | |
| 2008/0310692 A1 | 12/2008 | Robinson et al. | |
| 2009/0315987 A1 | 12/2009 | Straus | |
| 2010/0248281 A1 | 9/2010 | Straus | |
| 2013/0344522 A1 | 12/2013 | Ghirardi et al. | |

FOREIGN PATENT DOCUMENTS

PL          218010          5/2011

OTHER PUBLICATIONS

Lambert et al.,2001. A study of the minimum inhibitory concentration and mode of action of oregano essential oil, thymol and carvacrol Journal of Applied Microbiology, vol. 91, pp. 453-462.*
International Search Report for PCT/EP2014/060263 dated Jun. 18, 2014.
Banada, et al., "Label-free detection of multiple bacterial pathogens using light-scattering sensor", 2009, pp. 1685-1692, vol. 24, Biosensors and Bioelectronics.
Suchwalko, et al., "Bacteria species identification by the statistical analysis of bacterial colonies Fresnel patterns", May 6, 2013, pp. 11322-11337, vol. 21, No. 9, Optics Express.
Bae, et al, "On the sensitivity of forward scattering patterns from bacterial colonies to media composition", 2011, pp. 236-243, No. 4, J. Biophotonics.
Banada, et al., "Optical forward-scattering for detection of Listeria monocytogenes and other Listeria species", 2007, pp. 1664-1673, vol. 22, Biosensors and Bioelectronics.
Bae, et al., "Biophysical modeling of forward scattering from bacterial colonies using scalar diffraction theory", Jun. 10, 2007, pp. 3639-3648, vol. 46, No. 17, Applied Optics.
Buzalewicz, et al., "Influence of various growth conditions on Fresnel diffraction patterns of bacteria colonies examined in the optical system with converging spherical wave illumination", Oct. 24, 2011, vol. 19, No. 22, Optical Express.
Rajwa, et al., "Discovering the unknown: detection of emerging pathogens using a label-free light-scattering system", Dec. 2010, pp. 1103-1112, vol. 77, No. 12, Cytometry.

(Continued)

*Primary Examiner* — Blaine Lankford
(74) *Attorney, Agent, or Firm* — B. Aaron Schulman, Esq.; Stites & Harbison, PLLC

(57) ABSTRACT

The invention relates to a method for observing a sample (12), the sample (12) comprising a set of organisms (14), a solid substrate (16) supporting the set of organisms (14). The method being characterized in that the method includes steps for illuminating at least one portion of the sample (12) with a light beam, for acquiring a first diffraction pattern corresponding to an image of waves from the diffraction of the light beam by at least one portion of the set of organisms (14), for acquiring a second diffraction pattern corresponding to an image of waves from the diffraction of the light beam by at least one portion of the sample (12), for comparing the second diffraction pattern with the first diffraction pattern, for determining at least one characteristic relating to the set of organisms (14) from the result of the comparison step.

11 Claims, 8 Drawing Sheets

(56) References Cited

OTHER PUBLICATIONS

Bai, et al., "Development of a real-time system of monitoring bacterial colony growth and registering the forward-scattering pattern", Aug. 28, 2010, pp. 73150Z-1-73150Z-7, vol. 7315, Proc. of SPIE.
Bayraktar, et al, "Feature extraction from light-scatter patterns of Listeria colonies for identification and classification", May 2006, pp. 034006-1-8, vol. 11. No. 3, Journal of Biomedical Optics.
Bae, et al., "Analysis of time-resolved scattering from macroscale bacterial colonies", Jan./Feb. 2008, pp. 014010-1-8, vol. 13, No. 1, Journal of Biomedical Optics.

* cited by examiner

METHOD FOR OBSERVING ORGANISMS AND ASSOCIATED SYSTEM

The present invention relates to a method for observing organisms. The invention also relates to an associated system for observing organisms.

The invention is included in the field of microbiology and more specifically that of the identification of biological organisms and study of the interaction of the organisms with a medium.

Making cultures of organisms on particular media is known. These media are gelose nutritive media. These media give the possibility of increasing the number of sampled organisms, either specifically or by obtaining spatial separation of the different organisms making up the sample. Amplification in a specific way is obtained by the presence of inhibitors promoting the growth of certain organisms to the expense of others. Spatial isolation of different types of organisms is only obtained in the case of a polymicrobial sample.

One of the drawbacks of cultivation on such media is the time involved for obtaining from a single organism a set of organisms which may be observed and sampled by a human operator. This generally requires about 20 generations, i.e. a relatively long time of at least 24 hours.

Therefore there exists a need for a method for observing organisms in solid media, the application of which is more rapid than in the documents of the state of the art.

According to the invention, this object is achieved by a method for observing a sample, the sample comprising a set of organisms, a solid substrate supporting the whole of the organisms. The method includes a step for illuminating at least one portion of the sample with a light beam. The method also comprises a step for acquiring a first diffraction pattern corresponding to an image of waves from the diffraction of the light beam by a first portion of the set of organisms. The method also includes a step for acquiring a second diffraction pattern corresponding to an image of waves from the diffraction of the light beam by a second portion of the set of organisms. The method also comprises a step for comparing the second diffraction pattern with the first diffraction pattern and a step for determining at least one characteristic relative to the set of organisms from the result of the comparison step. The method comprises, during each acquisition step, a step for adapting the size of the light beam relatively to the size of the relevant portion of the set of organisms.

According to particular embodiments, the method comprises one or several of the following features, taken individually or according to any technically possible combination:

The set of organisms is located in a plane and each step for adapting the size of the light beam is applied in the plane so that the radius of the light beam in the plane is greater than or equal to 0.5 times the size of the relevant portion of the set of organisms and is less than or equal to 5 times the size of the relevant portion of the set of organisms.

Each step for adapting the size of the light beam is applied in the plane so that the radius of the light beam in the plane is greater than or equal to once the size of the relevant portion of the set of organisms, preferably greater than or equal to 3 times the size of the relevant portion of the set of organisms.

The first diffraction pattern is acquired at an instant different from that of the second diffraction pattern.

The first portion and the second portion are distinct.

The set of organisms is located in a plane and has a maximum extension along at least one direction, the radius of the light beam in the plane in the illumination step being comprised between one and five times the maximum extension of the set of organisms.

The solid substrate is able to grow at least one portion of the set of organisms and, at each instant, the radius of the light beam in the plane in the illumination step is maintained at a size comprised between three and five times the maximum extension of the set of organisms.

The solid substrate is able to grow at least one portion of the set of organisms and the sample comprises an area in which the solid substrate comprises an antibiotic, the second diffraction pattern corresponding to an image of waves from the diffraction of the light beam by the area of the sample and the feature determined in the determination step is the sensitivity of the organism to the antibiotic.

The solid substrate is able to grow at least one portion of the set of organisms and the sample comprises an area in which the solid substrate comprises an antibiotic, the concentration of which follows a gradient along one direction. The method includes a step for acquiring a plurality of diffraction patterns corresponding to an image of waves from the diffraction of the light beam by a plurality of portions of the area of the sample, the antibiotic concentration in each portion being different and a step for comparing each image of the plurality of images with the first image, the determined feature in the determination step being the minimum inhibiting concentration of the organism to the antibiotic.

The solid substrate is able to vary the optical index of at least one portion of the organisms of the set of organisms.

The solid substrate is a precipitating color-forming substrate.

The invention also relates to a system for observing a sample, the sample comprising a set of organisms, a solid substrate supporting the set of organisms, the observation system comprising a light source adapted so as to emit a light beam, a sample holder adapted for receiving the sample so that the sample is illuminated by the light beam which the light source is adapted to emit and so that the size of the light beam is adapted relatively to the size of the relevant portion of the set of organisms, a detection device adapted for acquiring diffraction patterns corresponding to an image of waves from the diffraction of the light beam by a portion of the sample and a computer adapted for comparing the diffraction patterns acquired by the detection device and for determining at least one characteristic relating to the set of organisms from the result of the comparison.

A method for observing a sample is also proposed, the sample comprising a set of organisms, a solid substrate supporting the set of organisms. The method includes the steps for illuminating at least one portion of the sample with a light beam, for acquiring a first diffraction pattern corresponding to an image of waves from the diffraction of the light beam by at least one portion of the set of organisms, for acquiring a second diffraction pattern corresponding to an image of waves from the diffraction of the light beam by at least one portion of the sample, for comparing the second diffraction pattern with the first diffraction pattern and for determining at least one characteristic relating to the set of organisms from the result of the comparison step.

According to particular embodiments, the method comprises one or several of the following characteristics, taken individually or according to any technically possible combination:

- The first diffraction pattern is acquired at an instant different from the second diffraction pattern.
- The first diffraction pattern corresponds to an image of waves from the diffraction of the light beam by a first portion of the sample, the second diffraction pattern corresponds to an image of waves from the diffraction of the light beam by a second portion of the sample, the first portion and the second portion being distinct.
- The set of organisms is located in a plane and has maximum extension along at least one direction, the radius of the light beam in the plane in the illumination step being comprised between one and five times the maximum extension of the set of organisms.
- The solid substrate is able to grow at least one portion of the set of organisms and, at each instant, the radius of the light beam in the plane in the illumination step is maintained to a size comprised between three and five times the maximum extension of the set of organisms.
- The solid substrate is able to grow at least one portion of the set of organisms and the sample comprises an area in which the solid substrate comprises an antibiotic, the second diffraction pattern corresponding to an image of waves from the diffraction of the light beam by the area of the sample and the determined characteristic in the determination step is the sensitivity of the organism to the antibiotic.
- The solid substrate is able to grow at least one portion of the set of organisms and the sample comprises an area in which the solid substrate comprises an antibiotic, for the concentration is monotonous along one direction. The method includes a step for acquiring a plurality of diffraction patterns corresponding to an image of waves from the diffraction of the light beam by a plurality of portions of the area of the sample, the antibiotic concentration in each portion being different and a step for comparing each image of the plurality of images with the first image, the characteristic determined in the determination step being the minimum inhibiting concentration of the organism to the antibiotic.
- The solid substrate is able to vary the optical index of at least one portion of the organisms of the set of organisms.
- The solid substrate is a precipitating color-forming substrate.

A system for observing a sample is also proposed, the sample comprising a set of organisms, a solid substrate supporting the set of organisms, the observation system comprising a light source adapted for emitting a light beam, a sample holder adapted for receiving the sample so that the sample is illuminated by the light beam which the light source is adapted for emitting, a detection device adapted for acquiring diffraction patterns corresponding to an image of waves from the diffraction of the light beam by at least one portion of the sample and a computer adapted for comparing the diffraction patterns acquired by the detection device and for determining at least one characteristic relating to the set of organisms from the result of the comparison.

Other features and advantages of the invention will become apparent upon reading the description which follows of embodiments of the invention, only given as an example and with reference to the drawings which are:

In the following, the notions of <<upstream>> and <<downstream>> are defined with reference to the direction of propagation of the light.

Figure 1:
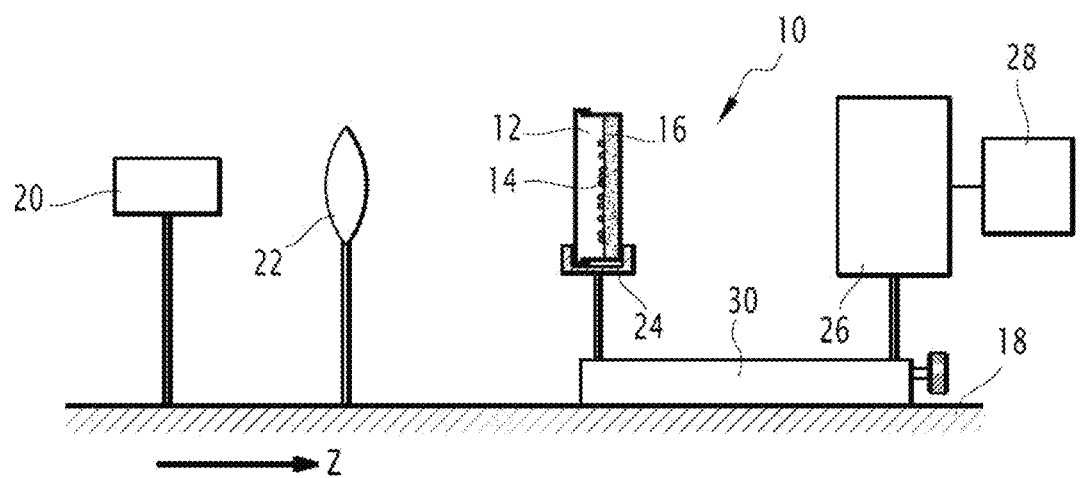
FIG. 1 is a schematic view of the system for observing biological species according to the invention.

The observation system 10 shown in FIG. 1 allows observation of a sample 12.

The sample 12 comprises a set of organisms 14 and a solid substrate 16 supporting the set of organisms 14.

Depending on the cases, an organism of the set of organisms 14 is acellular or cellular. Among cell organisms prokaryotic organisms and eukaryotic organisms are usually distinguished. *Archaea* (also called *Archaea* bacteria) and bacteria are examples of a prokaryotic organism. Eukaryotic organisms are either unicellular or pluricellular. As an example, protozoa, amoebae, algae or yeasts are unicellular eukaryotic organisms. Pluricellular eukaryotic organisms are cells for example from human and non-human mammals, from fungi, plants, protists or chromista.

By organisms, are for example meant microorganisms, in particular bacteria placed side by side, so as to form bacterial colonies. Thus, the organisms are distributed on the substrate 16 in different portions, each portion corresponding to one organism or to an agglomeration of organisms. Each portion may notably correspond to a bacterial colony. Subsequently, it is considered that the set of organisms 14 is located in a plane perpendicular to a horizontal axis Z.

Further, in this plane, the set of organisms 14 has maximum extension along one direction. By maximum extension, is meant a characteristic size of the set of organisms 14. For example this is the diameter of the circle in which is included the set of organisms 14. Generally, the invention applies to organisms or sets of organisms 14 for which the maximum extension is comprised between 100 nanometers (nm) and 1 millimeter (mm), preferably between 1 micrometer (µm) and 100 µm.

Thus, the invention in particular relates to the observation of bacterial colonies of a micrometric size, for which the characteristic size is less than 1 mm, for example comprised between 100 µm and 1 mm, or even between 50 µm and 500 µm. This allows observation at an early stage of the development of colonies. Time is then gained as compared with methods based on the observation of bacterial colonies of millimetric size.

The solid substrate 16 is able to grow at least one portion of the set of organisms 14. Thus, the substrate 16 is itself a culture medium or is placed in contact with a culture medium.

The solid substrate 16 is for example a gelose medium.

As an example, the solid substrate 16 is a Muller-Hinton 2 agar medium (noted as MH2 agar medium in the continuation of the description). Such a medium is adapted for producing antibiograms.

According to an alternative, the solid substrate 16 is only used as a biological adhesive.

As an example, the solid substrate 16 comprises polylysine or collagen of type I.

Figure 2:
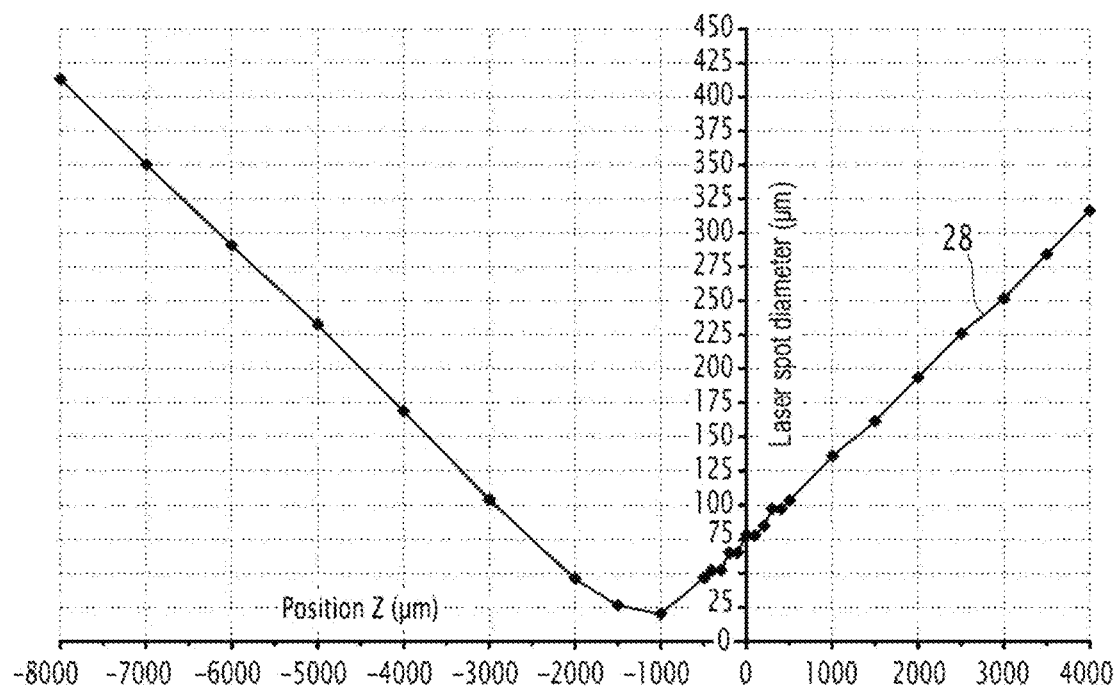
FIG. 2 is a graph illustrating the change in the radius of the laser beam versus the distance relatively to the sample of FIG. 1.

In the example of FIG. 2, the sample 12 appears as a Petri dish. A petri dish has a cylindrical shape, the base of which is a circle.

The observation system 10 is laid on an optical table 18 ensuring stability of the observation system 10.

The observation system 10 includes from upstream to downstream, a light source 20, an optical system 22, a sample holder 24 holding the sample 12, a detection device 26 and a computer 28.

According to the example of FIG. 1, the light source is a laser source 20, is able to emit a laser beam. According to an alternative, the light source 20 is a light emitting diode (often designated by the acronym of LED).

For example, the laser source 20 is a laser diode. In the example of FIG. 1, the laser beam emitted by the laser source 20 has a wavelength of 543.5 nm. Preferably, the light source 20 emits in a range of wavelengths comprised between 250 nm and 1,200 nm. Generally, the wavelength should be less than the maximum extension of the observed object, while allowing the use of usual detection means. Wavelengths in the range of visible light or the near infrared are then preferred. Alternatively, the wavelength of the laser beam is in a range of different wavelengths. The wavelength notably depends on the organism to be observed and on its sensitivity to illumination by a laser beam.

Further, the laser beam emitted by the laser source 20 has a power of less than 10 milliWatts (mW), and preferably less than 100 microWatts ($\mu$W) in order to avoid heating of the organisms when the organisms are illuminated with the laser beam.

The optical system 22 according to the example of FIG. 1 is a lens.

The characteristics of the optical system 22 as well as its positioning relatively to the laser source 20 are selected so that the radius of the laser beam in the plane including the set of organisms 14 is comprised between one and five times the maximum extension of the set of organisms.

Preferably, the characteristics of the optical system 22 as well as its positioning relatively to the laser source 20 are selected so that the radius of the laser beam in the plane including the set of organisms 14 is equal to three times the maximum extension of the set of organisms 14. It was ascertained that this gives the possibility of obtaining more contrasted images.

In the embodiment of FIG. 1, the spatial change in the radius of the laser beam upon exiting the optical system 22 is illustrated in FIG. 2.

The radius of a laser beam in a plane normal to the propagation axis of the laser beam is defined from the Gaussian profile of the intensity of the laser beam in the normal plane. The radius is defined as the half-width at $1/e^2$ of the intensity profile.

In the case of FIG. 2, the intensity of the laser beam was measured by a laser beam analyzer in different positions along the axis Z.

The plane Z=0 corresponds to the plane comprising the set of organisms 14.

The different points visible in FIG. 2 are connected through a curve 28 which is a Gaussian interpolation of the measured points. This interpolation shows that the waist of the laser beam upon exiting the optical system 22 is of 25 microns ($\mu$m) in the example of FIG. 1.

By definition, in the continuation of the description, the expression "size of a light beam" refers to the radius of the light beam, considered in the plane Z=0, the radius being as defined earlier. Respectively, the expression "size of a light beam" refers to the radius of the light beam considered in the plane Z=0, the radius being as defined earlier.

Further, the laser beam size in the plane including the set of organisms 14 is equal to 75 $\mu$m. Such a curve allows adjustment of the diameter of the incident laser beam according to the maximum extension of the observed object. The latter may be determined by an ancillary imaging device. Thus, preferably, the size of each observed object is determined before its observation, so as to adapt the size of the incident light beam. In the relevant example, the diameter of the laser beam is equal to three times said maximum extension. Such an adjustment allows adaptation of the beam relatively to the maximum extension of the observed object, while being aware that the latter may change over time.

On the other hand, such an adjustment is adapted to the successive observation of objects, of different sizes, positioned on the same substrate 16.

Thus, generally, the diameter of the incident light beam may be adapted to the size of the observed object.

Such an adaptation gives the possibility of having a diffraction pattern which may be utilized, regardless of the size of the observed objects. Indeed, if the size of the incident light beam is too large relatively to the observed object, the diffraction signal, specific to the object, is embedded in the too intense incident light signal. Conversely, if the size of the beam is too small relatively to the size of the object, the diffracted radiation is too little intense. Also, as indicated earlier, it is preferable to adapt the size of the beam so that the size of the light beam is comprised between 0.5 times and 5 times the size of the object to be characterized. Preferentially, the size of the light beam is adapted so that the size of the light beam is comprised between 3 times and 5 times the size of the object to be characterized.

Generally, each diffraction pattern is formed with a central area, around which extend concentric rings. When the size of the beam is adapted as described earlier, the rings are sufficiently numerous and contrasted for allowing accurate analysis of the diffraction pattern.

In the case of bacterial colonies, the size of the laser beam is of a few tens of microns, or even less than ten microns, in order to be able to observe colonies of small size, for example with a size comprised between 50 $\mu$m and 500 $\mu$m. The size of the laser beam is of a few millimeters when it is desired to observe larger micrometric colonies, for which the size is less than 1 mm.

According to an alternative, the optical system 22 is a lens with variable focal length, which also allows this adjustment.

The sample holder 24 gives the possibility of maintaining the sample 12 perpendicular to the axis Z, while maintaining it in the laser beam emitted by the laser source 20.

The detection device 26 is for example a CCD camera, CCD being the acronym of Charge-Coupled Device.

The detection device 26 is adapted for acquiring an image of waves from the diffraction of the laser beam emitted by the laser source 20 by at least one portion of the sample 12.

It is noted that there are no magnification optics between the sample 12 and the detection device 26.

In the invention, a diffraction pattern results from the interference of elastically scattered photons by the observed sample 12.

According to the example of FIG. 1, the detection device 26 and the sample holder 24 are integral with a displacement stage 30 which may be moved in a direction parallel to the Z axis.

The displacement stage 30 has a movement amplitude giving the possibility of ensuring at each instant, that the size of the laser beam comprising the set of organisms 14 is maintained at a size comprised between one and five times the maximum extension of the set of organisms 14.

The computer 28 is adapted for comparing diffraction patterns acquired by the detection device 26 and for determining at least one characteristic relating to the set of organisms 14 from the result of the comparison.

The operation of the observation system 10 will now be described with reference to several experiments conducted by the applicant and the results of which notably appear in FIGS. 3 to 25.

The first four experiments have an identical experimental procedure, only the way of analyzing and the selected organisms varying from one experiment to the other.

The solid substrate 16 is a MH2 agar medium.

Depending on the cases, the solid substrate 16 includes an antibiotic with increasing concentration when one moves away from the center of the Petri dish.

For example, such a gradient is obtained by depositing a disc impregnated with 30 micrograms (μg) of antibiotics.

The disc, as an illustration, is a disc with a diameter of 6.5 mm, the reference of which is 66548 in the Biorad Corporation.

When the disc is deposited at the surface of the substrate 16, an antibiotic concentration gradient is established, in the substrate 16, between the disc and the periphery of the substrate 16.

The antibiotic is gentamycin. gentamycin is an antibiotic from the family of aminosides or aminoglycosides. The antibiotics of this family are mainly used in the treatment of infections involving Gram bacteria—aerobic bacteria (*Pseudomonas*, *Acinetobacter* and *Enterobacter* for example).

Depending on the cases, the studied organisms belong to a strain sensitive to gentamycin or resistant to gentamycin.

The sensitive strain is of the *Escherichia coli* species with the ATCC number of 259922. In the continuation of the description, the sensitive strain is noted as EC10.

The minimum inhibitory concentration of the strain EC10 amounts to 1.0 μg/ml. In microbiology, the minimum inhibitory concentration (also noted with the acronym MIC) is the lowest concentration of antimicrobial agent which inhibits visible growth of an organism after one night of incubation.

The value of 1.0 μg/ml for the minimum inhibitory concentration was obtained by conducting an E-test®.

The principle of the E-test® is based on the combination of both concepts: Dilution and diffusion. The system E-test® comprises a non-porous plastic strip calibrated by a pre-established gradient of antibiotic concentration covering 15 dilutions for determining the MIC in μg/ml of a strain tested in a gelose medium.

The resistant strain is of the *Escherichia coli* species of ATCC number 35421. In the continuation of the description, the resistant strain is noted as EC21.

The minimum inhibitory concentration of the strain EC21 is greater than 256 μg/ml. This measurement was obtained by conducting an E-test®.

Thus, one has available a so-called sensitive strain (in this case EC10) and a so-called resistant layer (in this case EC21).

In each case, the sample 12 to be studied is prepared according to the following procedure.

At least one cell of the strain to be studied is cultivated on a trypticase soya gelose medium (often called TSA for <<Tryptic Soy Agar>>) for at least 24 hours.

A suspension of 5 milliliters (ml) comprising water and an amount of cells of the strain such that the turbidity of the solution is equal to 0.5 McF (McFarland standard), is then prepared.

The obtained suspension is diluted to $\frac{1}{1000}^{th}$ in water in a single step. In the relevant experiments, 3 ml of the suspension are poured into 3 ml of water.

A volume of 70 μl of the thereby obtained diluted suspension is then spread out by means of a rake on the solid MH2 agar substrate 16. Such a volume corresponds to the spreading of approximately 1,000 to 1,500 colonies on the solid substrate 16.

In the case when the experiment is conducted with a solid substrate 16 comprising the antibiotic gradient, the disc is applied immediately after the spreading step.

The whole of the sample 12 is then incubated for six hours at a temperature of 37° C. (Celsius).

After these six hours, the observation system 10 is used for applying a method for observing the cells of the sample 12.

For the first experiment, the studied organisms belong to the EC10 strain and the solid substrate 16 comprises a gentamycin gradient.

For the sake of clarity of the illustration, for each recorded diffraction pattern, the image in the direct space is also shown, this image not being useful for applying the observation method according to the invention.

A first colony of cells of the EC10 strain of the sample 12 is illuminated with the laser beam emitted by the laser source 20. The center of this colony is found at a distance of 13.5 millimeters (mm) from the center of the disc, in an area with low gentamycin concentration, since it is sufficiently far from the disc.

According to the example shown, in the plane of the sample 12, the illuminated area is three times larger than the area occupied by the observed organisms.

Figure 3:
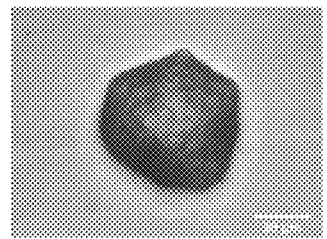
FIGS. 3 to 10, show experimental views of a first experiment for applying the organism observation method according to a first embodiment of the invention.

The image of the first colony in the direct space is visible in FIG. 3. The first colony is quite developed in size, the first colony occupying a substantially circular space with the diameter of about 60 μm. This indicates that the solid substrate 16 with a low gentamycin concentration does not sufficiently slow down the growth of the organisms.

Figure 4:
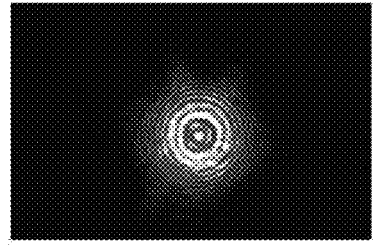

The detection device 26 then acquires a first diffraction pattern F1 corresponding to an image of waves from the diffraction of the laser beam by the first colony. FIG. 4 illustrates the obtained diffraction pattern F1.

A second colony of cells of the EC10 strain of the sample 12 is then illuminated with the laser beam emitted by the laser source 20. The center of this colony is found at a distance of 9.1 mm from the center of the disc, in an area with a gentamycin concentration greater than that of the imaged area in the case of FIGS. 3 and 4.

Figure 5:
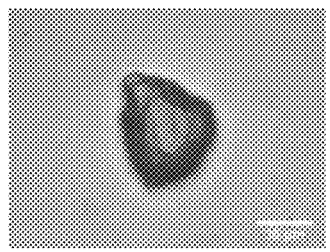

The image of the second colony in the direct space is visible in FIG. 5. The second colony is less developed in size than that of FIG. 3, the maximum size of the second colony is of about 50 μm. This shows the sensitivity of the organism EC10 to this gentamycin concentration.

Figure 6:
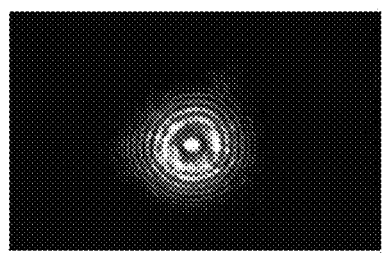

The detection device 26 then acquires a second diffraction pattern F2 corresponding to an image of waves from the diffraction of the laser beam by the second colony. FIG. 6 illustrates the obtained diffraction pattern F2.

A third colony of cells of the EC10 strain of the sample 12 is then illuminated with the laser beam emitted by the laser source 20. The center of this colony is found at a distance of 8.3 mm from the center of the disc, in an area with a gentamycin concentration greater than that of the imaged area in the case of FIGS. 5 and 6.

Figure 7:
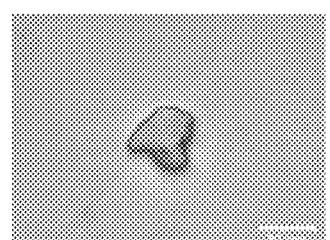

The image of the third colony in the direct space is visible in FIG. 7. The third colony is less developed in size than that of FIG. 5, the maximum size of the third colony being of about 30 μm. This shows good sensitivity of the organism EC10 to this gentamycin concentration.

Figure 8:
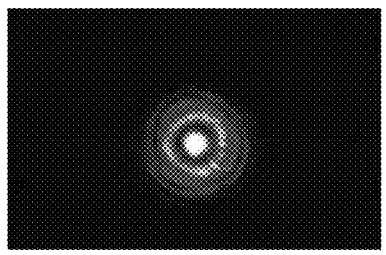

The detection device 26 then acquires a third diffraction pattern F3 corresponding to an image of waves from the diffraction of the laser beam by the third colony. FIG. 8 illustrates the obtained diffraction pattern F3.

A fourth colony of cells of the strain EC10 of the sample 12 is then illuminated with the laser beam emitted by the laser source 20. The center of this colony is found at a distance of 5.0 mm from the center of the disc, in an area with a gentamycin concentration greater than that of the imaged area in the case of FIGS. 7 and 8.

Figure 9:
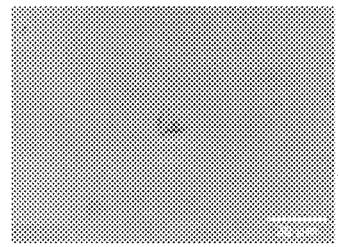

The image of the fourth colony in the direct space is visible in FIG. 9. The fourth colony is less developed in size than that of FIG. 7, the maximum size of the fourth colony is of about 15 μm. This shows good sensitivity of the EC10 organism to this gentamycin concentration.

Figure 10:
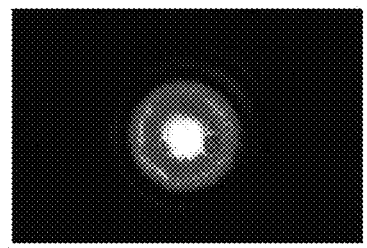

The detection device 26 then acquires a fourth diffraction pattern F4 corresponding to an image of waves from the diffraction of the laser beam by the fourth colony. FIG. 10 illustrates the obtained diffraction pattern F4.

Thus, on the same solid substrate, microcolonies are observed for which the diameter varies between 15 μm and 60 μm. As described earlier, if it is desired to have available a diffraction pattern which may be sufficiently utilized for each of these objects, the size of the incident light beam during each observation should be adapted to the size of each of these objects, the latter being determined beforehand.

This size adaptation is all the more important since, when the bacterial colonies are subject to an antibiotic, the resistant bacterial colonies continue their growth, while the other colonies are subject to the effect of the antibiotic. Therefore on the same substrate, a size variability of the objects to be characterized is therefore available.

The first diffraction pattern F1 is used as a reference diffraction pattern.

The second, third and fourth diffraction patterns F2, F3 and F4 are respectively compared with the first diffraction pattern F1.

According to an embodiment, the comparison is carried out visually by an observer.

When the diffraction pattern corresponds to a diffraction pattern, the comparison notably deals with the width of the central fringe, the number of observed fringes or the width of the secondary fringes.

As an example, by comparing the second diffraction pattern F2 and the first diffraction pattern F1, in particular it is observed that the central fringe and the secondary fringe are wider in the second diffraction pattern F2.

By comparing the fourth diffraction pattern F4 and the first diffraction pattern F1, it is observed that the central fringe and the secondary fringe are wider in the fourth diffraction pattern F4.

According to another embodiment, the comparison is carried out by means of a breaking down of the wave recorded by the acquisition device 26 into Zernike polynomials.

Each diffraction pattern F1, F2, F3 and F4 may thus be broken down into Zernike polynomials.

Preferably, the breaking down into Zernike polynomials is only carried out on the orders which are detectable by the detection device 26. This gives the possibility of limiting the computing time when the scattered wave is broken down into Zernike polynomials.

The coefficients of the obtained decomposition are then compared during the comparison.

From the result of the comparison, at least one characteristic relating to the whole of the organisms 14 is determined.

Within the scope of the first proposed experiment, two characteristics may be determined: the sensitivity of the organism to gentamycin i.e. the concentration from which gentamycin has an action on the organism.

Thus, with the observation method it is possible to observe organisms so as to infer therefrom characteristics relating to the organisms.

The first experiment shows how to determine the sensitivity of the organism to gentamycin, or even the concentration from which gentamycin has an action on the organism when the concentration of active ingredient (in this case gentamycin) to which the organism is exposed, is known. The correlation between the distance to the disc and the antibiotic concentration may notably be determined as a consistency line. Similarly, it is possible to identify the organism or to obtain early detection of Staphylococci aurei which are resistant to meticillin (also designated under the acronym of MRSA) or bacteria of the VRE (acronym of "Vancomycin resistant Enterococci") type and ESBL (acronym of "extended spectrum beta lactamase producing Enterobacteriaceae") type.

The characteristics relating to the organisms are obtained in 6 hours as compared with 48 hours for the techniques of the state of the art. Indeed, as it is possible to use diffraction patterns for identifying bacteria, the application of the invention does not involve a step for growing the sample taken before producing the antibiogram itself like this is the case in the methods of the state of the art.

The method therefore allows rapid detection of characteristics relating to organisms.

For the second experiment, the same experiment is conducted as the first experiment, by replacing the cells of the strain EC10 with cells of the strain EC21.

FIGS. 11 to 18 illustrate the second experiment.

Figure 11:
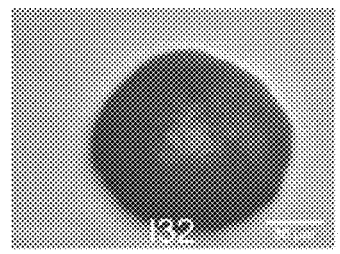
FIGS. 11 to 18 are experimental views of a second experiment for applying the organism observation method according to a first embodiment of the invention.
Figure 12:
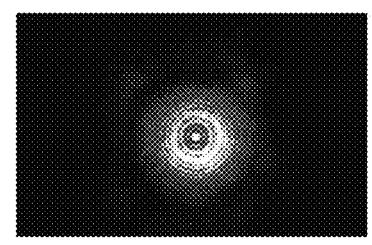

FIGS. 11 and 12 respectively correspond to the observation in direct space and of the diffraction pattern for a distance of 7.29 mm from the center of the disc.

Figure 13:
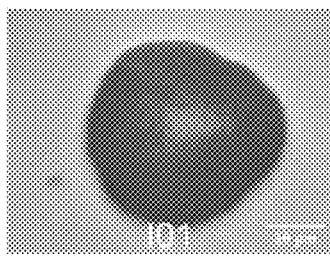
Figure 14:
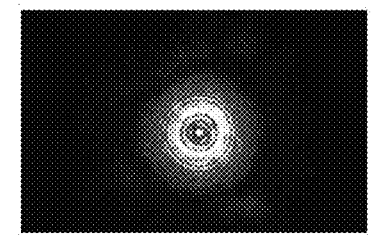

FIGS. 13 and 14 respectively correspond to the observation in direct space and of the diffraction pattern for a distance of 6.63 mm from the center of the disc.

Figure 15:
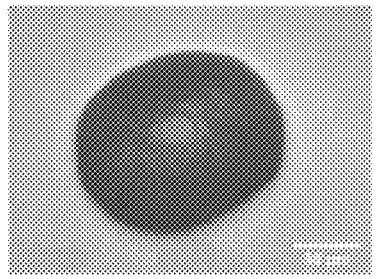
Figure 16:
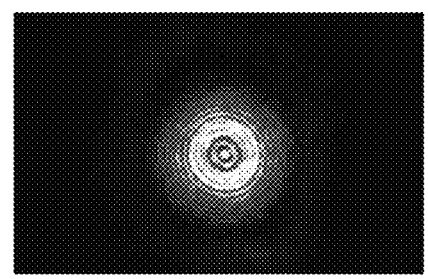

FIGS. 15 and 16 respectively correspond to the observation in direct space and of the diffraction pattern for a distance of 5.53 mm from the center of the disc.

Figure 17:
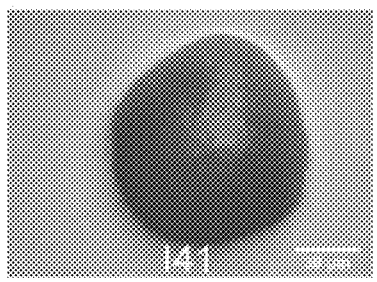
Figure 18:
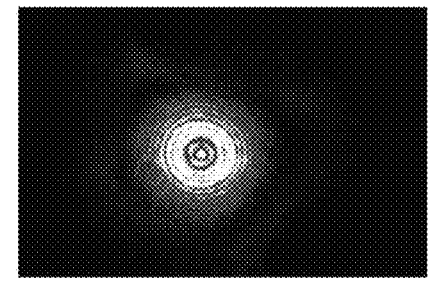

FIGS. 17 and 18 respectively correspond to the observation in direct space and of the diffraction pattern for a distance of 4.37 mm from the center of the disc.

Unlike the case of the diffraction patterns of FIGS. 4, 6, 8 and 10 relating to the first experiment, the diffraction patterns of FIGS. 12, 14, 16 and 18 are substantially identical while the gentamycin concentration is increasingly greater.

This actually shows that the organism EC21 is resistant to gentamycin.

This observation is compliant with the observation in the direct space of FIGS. 11, 13, 15 and 17. Indeed, the maximum extension of each observed colony is of the order of 90 μm. This indicates that the solid substrate 16 is suitable for growing EC21 organisms and that gentamycin has no effect on the growth of the EC21 organisms.

The first experiment and the second experiment shown correspond to a first embodiment, in which the first diffraction pattern corresponds to an image of waves from the diffraction of the laser beam by a first portion of the sample 12 (in this case here, the first colony) and the second diffraction pattern corresponds to an image of waves from the diffraction of the laser beam by a second portion of the sample 12 (in the case here, the second, the third or the fourth colony). The first portion and the second portion are distinct. In other words, in each of both experiments, four colonies are spatially distributed on the disc. This allows comparisons of the spatial type.

For the third experiment, a large number of diffraction patterns is acquired (about 100) for solid substrates 16 with and without gentamycin. The studied organism is a cell from the EC10 strain.

Further, the comparison step in the case of the third experiment is applied by means of a main component analysis conducted on the acquired diffraction patterns at the location of the visual observation or by analysis with breaking down into Zernike polynomials, suggested with reference to the first and second experiment.

Figure 19:
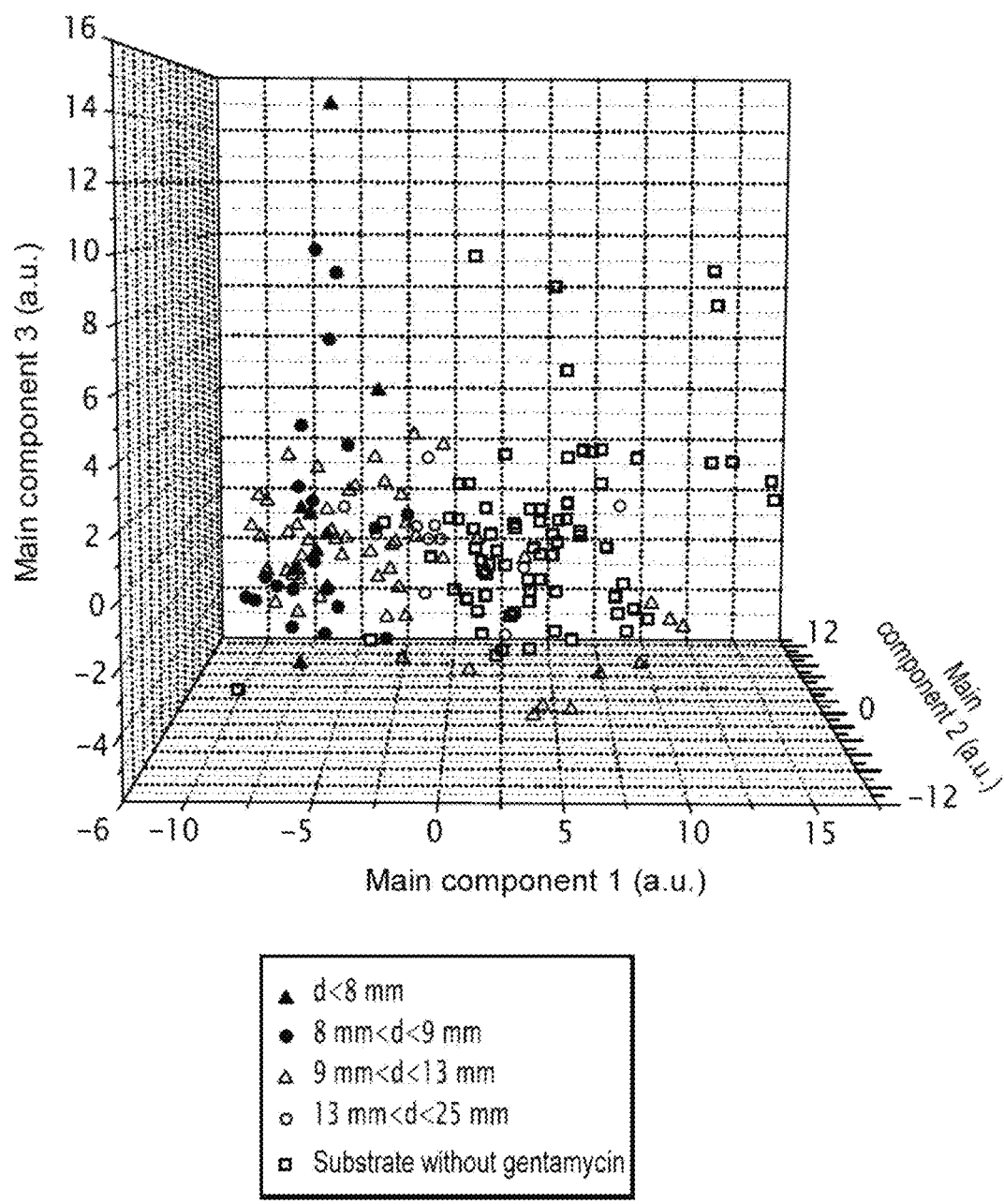
FIGS. 19 and 20 are illustrations of clouds of points obtained by a main component analysis conducted on diffraction patterns obtained within the scope of a third experiment for applying the organism observation method according to a first embodiment of the invention.
Figure 20:
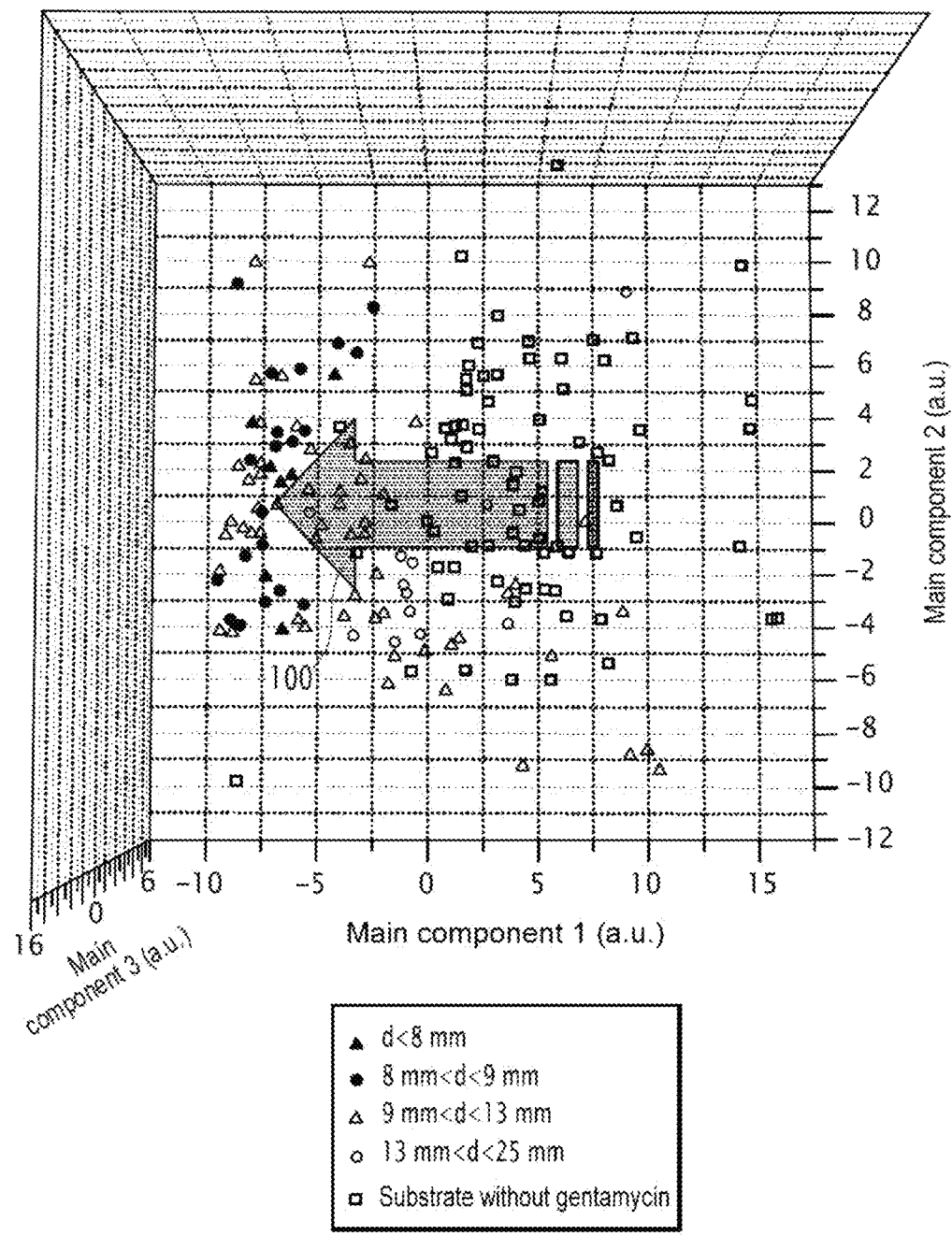

The result of the main component analysis obtained is illustrated in the views of FIGS. 19 and 20.

Each point is represented with three coordinates: Its value according to the first main component, its value according to the second main component and its value according to the third main component.

The square points correspond to the experiments conducted on a substrate without any gentamycin.

The points illustrated by a circle correspond to a distance d of the imaged organism to the center of the disc comprised between 13 mm and 25 mm. In this case, the gentamycin concentration is much less than the minimum inhibitory concentration of the EC10 strain.

The points illustrated by a triangle correspond to a distance d of the imaged organism to the center of the disc comprised between 9 mm and 13 mm. In this case, the gentamycin concentration is less than the minimum inhibitory concentration of the EC10 strain.

The points illustrated by a disc correspond to a distance d of the imaged organism to the center of the disc comprised between 8 mm and 9 mm. In this case, the gentamycin concentration is of the order of the minimum inhibitory concentration of the EC10 strain.

The points illustrated by a pyramid correspond to a distance d of the imaged organism to the center of the disc of less than 8 mm. In this case, the gentamycin concentration is greater than the minimum inhibitory concentration of the EC10 strain.

It is observed that the larger the concentration of gentamycin, the smaller is the value of the first main component. This is what is indicated by the arrow 100 in FIG. 20. This corresponds to the fact that the EC10 strain is a strain sensitive to gentamycin.

For the third experiment, the same experiment is conducted as the third experiment by replacing the cells of the strain EC10 with cells of the strain EC21.

Figure 21:
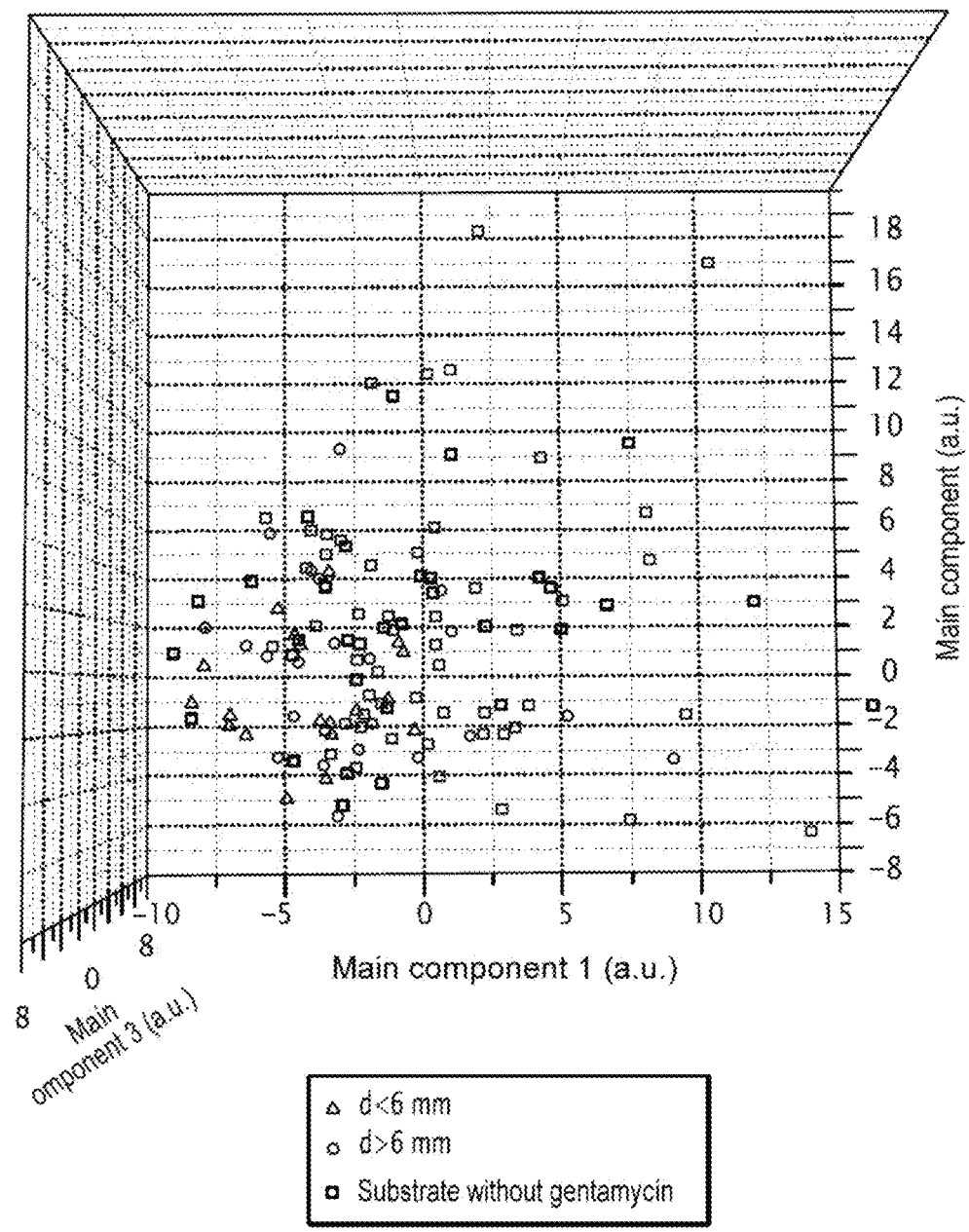
FIG. 21 is an illustration of the clouds of points obtained by a main component analysis conducted on diffraction patterns obtained within the scope of a fourth experiment for applying the organism observation method according to a first embodiment of the invention.

The result of the obtained main component analysis is illustrated in the view of FIG. 21.

The square points correspond to the experiments conducted on a substrate without any gentamycin.

The points illustrated by a circle correspond to a distance d of the imaged organism to the center of the disc greater than 6 mm. The points illustrated by a triangle correspond to a distance d of the imaged organism to the center of the disc of less than 6 mm In the case of FIG. 21, it is observed that the clouds of points in the presence and in the absence of an antibiotic overlap. This corresponds to the fact that the E21 strain is resistant to gentamycin.

According to a second embodiment, each acquired diffraction pattern is an image of the same organism taken at different instants.

FIGS. 22 to 25 illustrate this case, each diffraction pattern having been acquired at successive instants. In this case, the method is a time comparison method.

Figure 22:
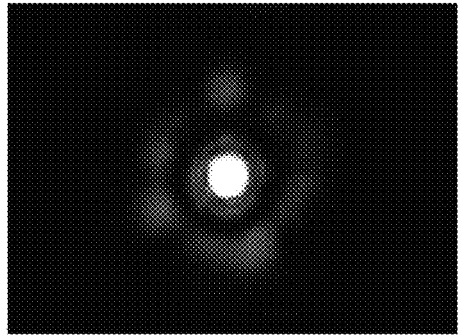
FIGS. 22 to 25 are views of diffraction patterns obtained by applying the method for observing biological species according to a second embodiment of the invention.
Figure 23:
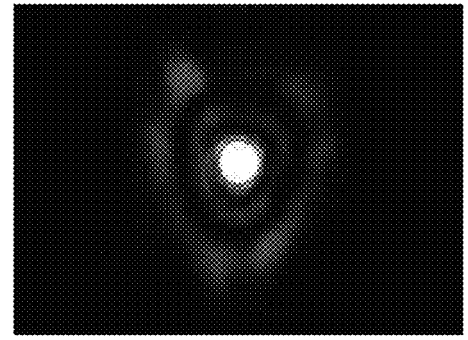
Figure 24:
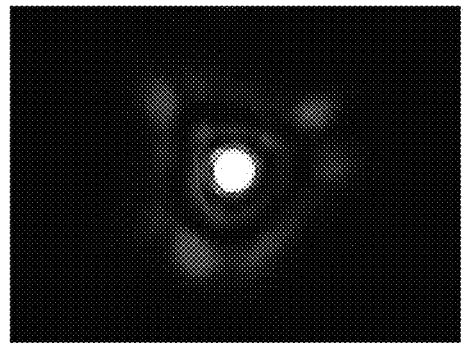
Figure 25:
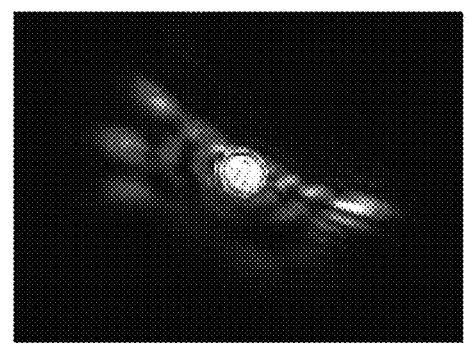

The modification of the diffraction pattern is visible by comparing the acquired diffraction pattern with the first acquired diffraction pattern (FIG. 22). The first diffraction pattern is then the reference pattern.

In this second embodiment, the effect of an antibiotic is demonstrated from the moment that it inhibits the growth of the studied organism.

The method of this second embodiment is therefore as rapid as possible since, as soon as the antibiotic has an effect, the method gives the possibility of obtaining the information that the organism is sensitive to the antibiotic.

Alternatively, the solid substrate 16 is able to vary the optical index of at least one portion of the organisms of the set of organisms 14. This gives the possibility of increasing the differences between the different diffraction patterns.

Thus, as an example, the solid substrate 16 includes precipitating color-forming substrates.

An indoxyl substrate is a type of precipitating color-forming substrate. Such substrates undergo hydrolysis leading to highly absorbent chromophores at the wavelength of the laser used for the diffraction.

The following Table 1 gives several examples of a precipitating color-forming substrate which may be used for the observation method of the invention.

Generally, any substrate able to generate by enzymatic hydrolysis an indoxyl or quinoline compound may be used for the observation method of the invention. Additionally, the shape of the substrate (a salt or a neutral compound) is indifferent provided that the hydrolysis capability is ensured.

According to an embodiment, the characterization of each diffraction pattern is preceded with a step for localizing the object to be studied and corresponding to said diffraction pattern. The localization is for example achieved by considerably increasing the size of the incident light beam, so that the latter illuminates a plurality of objects to be characterized, or even the whole of the solid substrate 16. The size of the light beam is then centimetric.

In such a configuration, according to the known principles of lens-less imaging, each object forms at the surface of the detection device 26, a diffraction pattern. This diffraction pattern does not allow accurate characterization, but is sufficient for localizing each object in the observed field. It is then possible to determine the coordinates of an object, so as to center the incident light beam on the latter, the size of the beam then being adapted to the dimensions of the object.

Thus, when a plurality of objects are dispersed on the substrate 16, it is possible to alternately illuminate the substrate 16 by means of a light beam allowing the formation of a plurality of diffraction patterns from the substrate 16 on the detection device 26, each diffraction pattern corresponding to an object, and identify the position of a diffraction pattern and center the incident light beam on this position, and reduce the size of the beam so that the size of the beam is adapted to the object, i.e. comprised between 0.5 times and 5 times the size of said object (preferably between once and 5 times the size of said object), this in order to form a sufficiently accurate diffraction pattern for allowing characterization of the object.

TABLE 1

| | Name of the substrate | Formula | Enzyme |
|---|---|---|---|
| FR<br>GB<br>CAS | 3-4-cyclohexenoesculetine β-D-galactopyranoside<br>3,4-Cyclohexenoesculetin β-D-galactopyranoside<br>182805-65-8 | | β-galactosidase |
| FR<br>GB<br>CAS | Sel de sodium du 5-Bromo-4-chloro-3-indolyl β-D-glucuronide<br>5-Bromo-4-chloro-3-indolyl β-D-glucuronide sodium salt<br>129541-41-9 | | glucuronidase |
| FR<br>GB<br>CAS | acétate de 5-bromo-4-chloro-3-indolyle<br>5-bromo-4-chloro-3-indolyl acetate<br>3252-36-6 | | esterase |
| FR<br>GB<br>CAS: | 5-bromo-4-chloro-3-indolyl butyrate<br>5-Bromo-4-chloro-3-indolyl butyrate<br>129541-43-1 | | lipase |
| FR<br>GB<br>CAS: | Sel de disodium du 5-bromo-4-chloro-3-indolyl phosphate<br>5-Bromo-4-chloro-3-indolyl phosphate disodium salt<br>102185-33-1 | | phosphatase |
| FR<br>GB<br>CAS | 6-Chloro-3-indolyl α-D-galactopyranoside<br>6-Chloro-3-indolyl α-D-galactopyranoside<br>198402-61-8 | | galactosidase |

TABLE 1-continued

| Name of the substrate | | Formula | Enzyme |
|---|---|---|---|
| FR | 6-Chloro-3-indolyl β-D-glucopyranoside | | glucosidase |
| GB | 6-Chloro-3-indolyl β-D-glucopyranoside | | |
| CAS | 159954-28-6 | | |

For each example of a precipitating color-forming substrate, are successively given its names in French and in English as well as its CAS number (second column), its chemical formula (third column) and the enzyme on which the substrate is effective (fourth column). The substrates forming quinoline, such as 8-hydroxyquinoline-β-D-glucuronide at the bottom of the table, require the presence of a chelating metal, such as ferrous ions, in order to induce the formation of an insoluble colored product.

The invention claimed is:

1. A method for observing a sample comprising:
providing a solid substrate supporting a set of organisms being located in a plane,
illuminating at least partially the sample with a first light beam emitted by a light source adapted for emitting a light beam propagating along a propagation direction, the plane in which the set of organisms is located being perpendicular to the propagation direction, the part of the sample being illuminated by the first light beam comprising a first portion of the set of organisms,
acquiring a first diffraction pattern with a detection device adapted to acquire diffraction patterns, the first diffraction pattern corresponding to an image of waves from the diffraction of the first light beam by the first portion of the set of organisms, wherein a diameter is defined for the first portion of the set of organisms in said plane and named first diameter, the acquiring of the first diffraction pattern comprising adapting the radius of the first light beam so that the radius of the first light beam in said plane is greater than or equal to 1 times the first diameter and less than or equal to 5 times the first diameter,
illuminating partially the sample with a second light beam emitted by the light source, the part of sample illuminated by the second light beam comprising a second portion of the set of organisms,
acquiring a second diffraction pattern with the detection device, the second diffraction pattern corresponding to an image of waves from the diffraction of the second light beam by the second portion of the set of organisms, wherein a diameter is defined for the second portion of the set of organisms in said plane and named second diameter, the acquiring of the second diffraction pattern comprising adapting the radius of the second light beam so that the radius of the second light beam in said plane is greater than or equal to 1 times the second diameter and less than or equal to 5 times the second diameter,
using a computer to compare the second diffraction pattern with the first diffraction pattern so as to obtain a result of the comparison, and
using a computer to determine at least one characteristic relating to the set of organisms from the result of the comparison.

2. The method according to claim 1, wherein the radius of the first light beam in said plane is greater than or equal to 3 times the first diameter and less than or equal to 5 times the first diameter.

3. The method according to claim 1, wherein the first diffraction pattern is acquired at a different time from that of the second diffraction pattern.

4. The method according to claim 1, wherein the first portion and the second portion are distinct.

5. The method according to claim 1, wherein the first portion of the set of organisms is included in a circle having the first diameter, and the second portion of the set of organisms is included in a circle having the second diameter.

6. The method according to claim 5, wherein the radius of the first light beam and the second light beam in the plane during illumination is maintained between three and five times the maximum extension of the set of organisms.

7. The method according to claim 1, wherein the sample comprises an area in which the solid substrate comprises an antibiotic, wherein the second diffraction pattern corresponds to an image of waves from the diffraction of the light beam by the area of the sample, and wherein the characteristic determined is the sensitivity of the organism to the antibiotic.

8. The method according to claim 1, wherein the sample comprises an area in which the solid substrate comprises an antibiotic having a concentration that follows a gradient along one direction, and where the method further comprises:
acquiring a plurality of diffraction patterns corresponding to an image of waves from the diffraction of the light beam by a plurality of portions of the area of the sample, the antibiotic concentration in each portion being different, and
comparing each image of the plurality of diffraction patterns with the first image obtained according to the first diffraction pattern according to claim 1,
wherein the characteristic determined is the minimum inhibitory concentration of the antibiotic that will inhibit growth of the set of organisms.

9. The method according to claim 1, wherein the solid substrate is able to vary the optical index of at least one portion of the set of organisms.

10. The method according to claim 9, wherein the solid substrate is a precipitating color-forming substrate.

11. The method according to claim 1, wherein, the radius of the second light beam in said plane is greater than or equal to 3 times the second diameter and less than or equal to 5 times the second diameter.

* * * * *